United States Patent
McAuley et al.

(10) Patent No.: US 9,205,215 B2
(45) Date of Patent: Dec. 8, 2015

(54) NASAL PILLOWS WITH HIGH VOLUME BYPASS FLOW AND METHOD OF USING SAME

(75) Inventors: Alastair Edwin McAuley, Auckland (NZ); Ian Douglas Makinson, Auckland (NZ); Fiona Elizabeth Cresswell, Auckland (NZ)

(73) Assignee: FISHER & PAYKEL HEALTH LIMITED, Auckland (NZ)

( * ) Notice: Subject to any disclaimer, the term of this patent is extended or adjusted under 35 U.S.C. 154(b) by 738 days.

(21) Appl. No.: 12/742,172

(22) PCT Filed: Nov. 14, 2008

(86) PCT No.: PCT/NZ2008/000307
§ 371 (c)(1),
(2), (4) Date: Dec. 28, 2010

(87) PCT Pub. No.: WO2009/064202
PCT Pub. Date: May 22, 2009

(65) Prior Publication Data
US 2011/0114098 A1 May 19, 2011

(30) Foreign Application Priority Data

Nov. 16, 2007 (NZ) ........................................ 563497

(51) Int. Cl.
*A61M 16/00* (2006.01)
*A61M 16/06* (2006.01)
(Continued)

(52) U.S. Cl.
CPC ........... *A61M 16/0666* (2013.01); *A61M 16/06* (2013.01); *A61M 16/0683* (2013.01);
(Continued)

(58) Field of Classification Search
CPC .................... A61M 16/0666; A61M 16/0672; A61M 16/0677; A61M 16/0841; A61M 16/085; A61M 16/0858; A61M 2016/0027; A61M 2210/0618

USPC ............ 128/203.22, 204.18, 204.21, 204.26, 128/206.11, 207.18
See application file for complete search history.

(56) References Cited

U.S. PATENT DOCUMENTS

| | | | | |
|---|---|---|---|---|
| 3,884,223 | A * | 5/1975 | Keindl | 128/206.11 |
| 4,054,133 | A * | 10/1977 | Myers | 128/204.26 |

(Continued)

FOREIGN PATENT DOCUMENTS

| | | |
|---|---|---|
| EP | 1275412 | 1/2003 |
| EP | 1787670 A2 | 11/2006 |
| WO | WO2007033347 | 3/2007 |

OTHER PUBLICATIONS

Written Opinion of the International Searching Authority, May 28, 2009.

(Continued)

*Primary Examiner* — Justine Yu
*Assistant Examiner* — Michael Tsai
(74) *Attorney, Agent, or Firm* — Knobbe, Martens, Olson & Bear LLP

(57) ABSTRACT

A fan unit which in use forms part of a gases supply unit, the gases supply unit suitable for use as part of a system for providing heated humidified gases to a user, the fan unit having a casing that has an inlet aperture and an outlet passage, the outlet passage including an exit aperture, the fan unit also including a fan which is located inside the casing and which is adapted for connection to a motor to drive rotation of the fan in use, the fan drawing gases into the casing via the inlet aperture, and forcing these gases out of the casing via the outlet passage as a gases stream, the outlet passage further including at least one bypass vent hole independent of the exit aperture and arranged at an angle to the path of the gases stream through the outlet passage.

19 Claims, 11 Drawing Sheets

(51) Int. Cl.
*A61M 16/08* (2006.01)
*A61M 16/16* (2006.01)

(52) U.S. Cl.
CPC .......... *A61M16/0858* (2014.02); *A61M 16/16* (2013.01); *A61M 2016/0027* (2013.01); *A61M 2016/0033* (2013.01); *A61M 2210/0618* (2013.01)

(56) References Cited

U.S. PATENT DOCUMENTS

| | | | | |
|---|---|---|---|---|
| 4,989,599 | A * | 2/1991 | Carter | 128/207.18 |
| 5,099,836 | A * | 3/1992 | Rowland et al. | 128/204.23 |
| 5,107,831 | A * | 4/1992 | Halpern et al. | 128/204.26 |
| 5,134,995 | A * | 8/1992 | Gruenke et al. | 128/204.23 |
| 5,245,995 | A * | 9/1993 | Sullivan et al. | 128/204.23 |
| 5,865,174 | A * | 2/1999 | Kloeppel | 128/204.23 |
| 5,953,713 | A * | 9/1999 | Behbehani et al. | 706/16 |
| 6,123,074 | A * | 9/2000 | Hete et al. | 128/205.11 |
| 6,526,974 | B1 * | 3/2003 | Brydon et al. | 128/205.24 |
| 6,662,803 | B2 * | 12/2003 | Gradon et al. | 128/205.25 |
| 6,684,882 | B1 * | 2/2004 | Morine | 128/206.11 |
| 6,799,575 | B1 | 10/2004 | Carter | |
| 7,086,399 | B2 * | 8/2006 | Makinson et al. | 128/204.21 |
| 7,856,979 | B2 * | 12/2010 | Doshi et al. | 128/206.11 |
| 2002/0112730 | A1 * | 8/2002 | Dutkiewicz | 128/207.18 |
| 2003/0079749 | A1 * | 5/2003 | Strickland et al. | 128/203.22 |
| 2003/0130591 | A1 | 7/2003 | Starr et al. | |
| 2005/0005935 | A1 * | 1/2005 | Gradon | 128/204.18 |
| 2006/0002734 | A1 | 1/2006 | Daniels | |
| 2006/0042638 | A1 * | 3/2006 | Niklewski et al. | 128/207.18 |
| 2007/0095347 | A1 * | 5/2007 | Lampotang et al. | 128/204.23 |
| 2007/0113847 | A1 | 5/2007 | Acker et al. | |

OTHER PUBLICATIONS

Australian Patent Examination Report No. 2; dated Mar. 19, 2014; 4 pages.

* cited by examiner

NASAL PILLOWS WITH HIGH VOLUME BYPASS FLOW AND METHOD OF USING SAME

This application is a U.S. National Phase filing of PCT/NZ2008/000307, having an International filing date of Nov. 14, 2008 which was published in English on May 22, 2009 under International Publication Number WO 2009/064202 which claims the priority of New Zealand 563497, filed on Nov. 16, 2007. These applications are hereby incorporated by reference in their entirety.

BACKGROUND OF THE INVENTION

1. Field of the Invention

This invention relates to devices for providing a flow of gases at a pressure above atmospheric pressure to a user for therapeutic purposes.

This invention also relates to patient interfaces for use with devices which provide a gases stream at a pressure above atmospheric to a user for therapeutic purposes.

This invention also relates to methods of using patient interfaces of known geometry and dimensions to provide improved real time adjustment of the characteristics of a gases stream provided to a user for therapeutic purposes.

This invention also relates to methods of using patient interfaces of known geometry and dimensions to improve the initial or in-use characteristics of a gases stream provided to a user for therapeutic purposes.

2. Summary of the Prior Art

Devices or systems for providing a humidified gases flow to a patient for therapeutic purposes are well known in the art. Systems for providing therapy of this type, for example CPAP therapy, have a structure where gases at a pressure above atmospheric are delivered from a blower (also known as a compressor, an assisted breathing unit, a fan unit, a flow generator or a pressure generator) to a humidifier chamber downstream from the blower, where they are heated and humidified, and then provided to a user via a user interface. Examples of commonly used interfaces are:

1) a full face mask,
2) a nasal mask (covering the entire nose),
3) an oral mask sealing onto the mouth,
4) nasal pillows (a pair of conduits which provide a gases stream to a user through the users nostrils, contacting and sealing around the flares of the user),
5) a nasal cannula (a pair of narrow-bore conduits that pass into the nostrils of a user without sealing on the nares),
6) a combination of the above.

Other forms of interface can be used—for example tracheostomy fittings or similar. However, these are less common than those listed above.

Generally, the interface is connected to an outlet of the humidifier by a flexible conduit or similar. The interface is usually held in position on a user's head by a headgear. It is common to make at least part of the headgear from soft adjustable straps, for example Neoprene or similar.

Interfaces used with CPAP devices are provided with a leak path known as a bias flow which has the purpose of venting exhaled air to atmosphere. This prevents the patient re-breathing carbon dioxide contained in the exhaled breath. For example, the Flexifit 432 full face mask includes a number of small holes in the shell of the mask passing from the inside to the outside to act as bias vent holes.

CPAP therapy is intended to provide a fixed-pressure or constant pressure to a user. However, in reality, it is almost impossible to provide a fixed pressure for all flow levels. Variations on basic CPAP blowers have been introduced over time in order to address shortcomings.

For example, some blowers are adapted so as to provide VPAPυ or BiPAP® (Variable/Bilevel Positive Airway Pressure) where two levels of pressure are provided by the blower: one for inhalation (IPAP) and a lower pressure during exhalation (EPAP).

Ramping is possible with some blowers. This is a method used at the beginning of a users sleep cycle to allow the user to fall asleep more easily. The pressure provided by the blower at the start of a sleep cycle is lower than what is ideally required. The pressure provided by the blower is gradually increased to the prescribed level over a period of time, allowing the user to fall asleep before the full pressure is applied.

A blower that provides exhalation pressure relief is adapted so that there is a short drop in pressure during exhalation to reduce the effort required by a user to exhale. This feature is known by the trade name C-Flex® in some blowers manufactured by Respironics, and by the trade name EPR™ in the machine manufactured by ResMed.

Another disadvantage that some users can experience when using a mask as their interface is as follows: when the user exhales against an incoming pressurised stream of gases, this can cause leaks around the edges of the mask as the mask partially lifts away from, or is pushed off, the surface of a user's face. This can cause a user to wake up as gases wash across their face or jet into their eyes. It can also affect the efficiency of the treatment as not all the gas provided by the blower is reaching the user (some escapes before it reaches the user). In response to mask leak, it is common for a user or health professional to tighten the straps of the headgear. This can lead to the mask feeling uncomfortable for a user and with time can cause pressure sores and/or soft-tissue abrasions at the nasal bridge. The user can in response discontinue their therapy, or at least be unfavourably inclined towards continuing.

It should also be noted that uncontrolled mask leak is undesirable and a great deal of effort has been put into measuring and minimising mask leak, with the preferred intention of eliminating it entirely. One way of helping to avoid mask leak is to add a one-way or bias valve to the system, on or close to the mask or interface. This allows exhaled gases to be intentionally vented to atmosphere, and helps to avoid leak around the edges of a mask or other sealed interface. A mask vent is described in U.S. Pat. No. 6,662,803. A mask vent of different design is described in EP 1275412. Several other solutions have also been suggested. These can be used either alone or for example in tandem with mask vents or other solutions. U.S. Pat. No. 6,123,074 discloses a system where the mask includes a suitable exhaust port, and where pressure in the breathing system is constantly monitored and a pressure controller downstream of the flow generator (between the mask and the flow generator) acts to maintain a constant pressure within the conduit. U.S. Pat. No. 6,526,974 discloses a CPAP device where the size of the inlet to the blower or flow generator can be varied, or where the size of the inlet is automatically varied, in response to the needs of the user. An exhalation path is provided so that the back pressure in the system is limited.

If the mask or patient interface is provided with bias vent holes, there is always going to be some level of leakage through the vent holes. A typical level of exhaust flow through bias vent holes in a mask is in the region of 35 Liters per minute, at a pressure level of 10 cmH.sub.2O above atmospheric pressure. This is a known level of leak and can be compensated for by adjusting the settings of the blower and the humidifier. However, a portion of the heated, humidified gases is lost (sacrificed) before reaching the user.

In contrast, one advantage of using a nasal cannula is that all the flow is provided to the nostrils and does not vent (through bias vent holes) before reaching the nasal cavity. However, unsealed nasal cannulas have their own shortcomings. For example, the size of the space between the nostrils and the cannula is unknown. Therefore, the amount of leak from around the cannula is unknown and uncontrollable, even when the pressure at the cannula is known, and the pressure delivered to the nares is unknown or uncontrollable even if the flow delivered to the cannula is known. Also, when using a cannula, it is impossible to avoid the entrainment of dry, unheated atmospheric air into the nostrils of a user.

Another problem encountered with unsealed high flow nasal cannula is the noise that is generated by air flowing between the nares and the outside of the nasal cannula. This can be especially problematic when a nearly constant flow is provided to the user. In this situation the flow exiting to atmosphere varies significantly as the patient exhales and inhales creating noise that varies in intensity over the breath cycle. The amount of noise is strongly dependant on the position and orientation of the cannula in nares as this affects the velocity of the exhaust (leaked) gas.

High flow nasal cannula are used to provide gas for treatment of illnesses including COPD, CF and OSA amongst many others. It is sometimes desirable to set a flow rate through the cannula that is sufficient to meet the patient's maximum inspiratory demand, but which does not significantly exceed that required to meet maximum inspiratory demand. This can be difficult to achieve reliably due to the unknown resistance to flow of air passing between outside of the cannula and the inside of the nares.

For treatment of some conditions the pressure at the nares is important. For example, in the treatment of some respiratory conditions, such as COPD, application of pressure during expiration can be beneficial. With a non-sealing nasal cannula the amount of pressure delivered is unknown as explained previously.

Nasal pillows are a variation on the basic cannula structure which are intended to go some way toward solving the problems which are experienced with nasal cannulas. In nasal pillows, the narrow elongated inlet portions of the cannula are replaced with soft flexible portions which generally conform to the geometry of a users nostrils, and which flex to seal against the nares of a user in use. This helps to avoid entrainment of atmospheric air into the nostrils of a user when inhaling. However, it can be difficult to exhale against the stream of air provided when using nasal pillows, and uncontrolled leaks can occur. It can also be difficult to create an adequate seal against the nares if the users nasal geometry is significantly different from that of the pillows.

Further disadvantages arise when attempting to measure the flow and the pressure at various points in the system. It can be difficult to relate actual measured data to the breathing cycle of a user in order to monitor or adjust (either manually or automatically through a feedback mechanism in the blower control circuitry) controllable system parameters such as the fan speed (to alter flow and pressure) or the energy provided to the heater mechanism of the humidifier (to alter the temperature and humidity of the gases) in order to provide the most effective therapy. It is especially difficult to accurately assess pressure and flow e.g. in the upper airway of a user when leaks occur between the face or nose of the patient and the interface.

Other forms of treatment deliver a high flow of gas (dry or humidified) through an unsealed interface such as a nasal cannula. In these applications there is a large leak out of the nostrils around the nasal cannula. The large leak means that the pressure in the airway is relatively low compared to CPAP treatment.

A disadvantage of the high flow nasal cannula system is that it is especially difficult to assess the values of pressure and actual patient flow during a patient's breath because the resistance to flow for gas passing between the cannulae and the nares can be variable depending on the position of the cannula and shape and size of the nare.

Obstructions in some patients' airways during sleep can cause limited airflow, leading to apnoea, hypopnoea, or snoring. The obstruction is often a collapsed pharynx. The obstruction may be a partial airway obstruction, leading to altered characteristics of the airflow. A hypopnoea is a reduction of flow that is greater than 30%, but less than 90% of baseline, for a period of at least 10 seconds and which is accompanied by oxygen desaturation greater than 4% from baseline. An apnoea is similar but airflow is reduced by greater than 90% from baseline. Each of these conditions frequently leads to sleep deprivation.

It is well known to treat patients suffering from sleep deprivation with positive airway pressure therapy ("PAP"). This therapy can be Continuous Positive Airway Pressure ("CPAP"), Variable Positive Airway Pressure ("VPAP"), Bi-level Positive Airway Pressure ("BiPAP"), or any of numerous other forms of respiratory therapy. The application of positive pressure to the patient's pharynx helps minimize or prevent this collapse. Positive airway pressure therapy is currently applied by means of an apparatus containing a pressure source, typically a blower, through a tube to a mask, which the patient wears in bed.

It is desired to control the applied pressure. Too little pressure tends not to solve the problem. Too much pressure tends to cause discomfort to the patient, such as drying out of the mouth and pharynx, as well as difficulty in exhaling against the applied pressure. The difficulty in applying optimum pressure is that incidents of airway obstruction come and go through the course of a night's sleep. One solution is to try to find an optimum pressure for a particular patient and maintain that pressure. This method requires the patient's stay at a sleep clinic, where sleep specialists can monitor the patient's course of breathing throughout one or more night's sleep, prescribe the appropriate pressure for that patient, and then set the apparatus to deliver the appropriate pressure. This method is, of course, inconvenient as well as expensive to the patient and tends to be inaccurate, as a typical patient will not sleep the same when away from familiar bedding and surroundings.

Accordingly, it is desirable to be able to adjust the applied pressure without requiring the patient to attend at a sleep centre. Devices which are aimed at adjusting the applied pressure automatically are generally known as 'Auto adjusting Devices'. Various methods of in-home adjustments have been considered. One method generally thought to be effective is to monitor the patient to try to anticipate the onset of an obstructed airway, and to adjust the pressure in response. When an elevated upper airway resistance or flow obstruction is anticipated or underway, the apparatus increases the applied pressure. When the patient returns to normal sleep, the applied pressure is reduced. The problem then, is to determine when a flow obstruction is occurring or is about to occur. It is desired to anticipate correctly in order to avoid the problems set forth above for when too much or too little pressure is applied.

Various methods have been proposed to solve this problem. In U.S. Pat. No. 5,107,831 to Halpern, an apparatus monitors the airflow to the patient and posits an event of airway obstruction when the patient's breath fails to meet a predetermined threshold of flow rate or duration. In U.S. Pat. No. 5,134,995 to Gruenke, an apparatus monitors the airflow to the patient and analyzes the shape of the flow versus time waveform. If the shape of this waveform tends to be flattened, that is, more similar to a plateau than to a sinusoid, the apparatus posits an event of airway obstruction. In U.S. Pat. No. 5,245,995 to Sullivan, an apparatus monitors the patient's sound with a microphone. If audible snores are detected, the apparatus posits an event of airway obstruction. Similarly, in U.S. Pat. No. 5,953,713 to Behbehani, an apparatus measures the total pressure within an interface placed over a patient's airway and inputs frequency data in the range 100 to 150 Hz into a neural network to determine the presence of a pharyngeal wall vibration (a snore) which, according to Behbehani, is a precursor to sleep disorder breathing.

An alternative method described in patent US20060027234A1: Auto-titrating method and apparatus. This specification discusses obtaining information from the frequency range of zero to 25 HZ in the frequency domain of the flow, and adjusting the pressure based on the information obtained.

Prior art methods have not proven totally satisfactory in controlling the applied pressure during PAP therapy. For example, the '713 patent, by measuring in the range of 100 to 150 Hz, essentially tests for snoring and does not measure or analyze any information concerning partial airway obstruction, as this information is found in the lower frequency range 0 to 25 Hz.

It is an object of the present invention to provide a breathing assistance apparatus which goes some way to overcoming the abovementioned disadvantages or which at least provides the public or industry with a useful choice.

DISCLOSURE OF THE INVENTION

In a first aspect the invention may broadly be said to consist in a user interface for use as part of a system for providing gases to a patient for therapeutic purposes, said system of the type that includes a gases supply conduit which in use provides a gases stream, said patient having nares, said user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent one of said nares of said patient, each one of said pair of nasal pillows divided into three separate passages, each of said passages sealed from the other passages at least within said pillows, the first one of said passages configured to act in use as a gases delivery passageway and connected to said main body so that in use gases from said conduit can pass along said first passage to said patient, the second one of said passages configured to act as a pressure measurement duct in use, and the third one of said passages open to atmosphere and adapted to act as a high-flow bypass passage.

In a second aspect the invention may broadly be said to consist in a user interface for use as part of a system for providing gases to a patient for therapeutic purposes, said system of the type that includes a gases supply conduit which in use provides a gases stream, said patient having nares, said user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent nare of said patient, each one of said pair of nasal pillows divided into two separate passages, each of said passages in each pillow sealed from the other, the first one of said passages configured as a gases delivery passageway and connected to said main body so that in use gases from said gases stream pass along said first passage to said patient, the second one of said passages open to atmosphere and adapted to act as a high-flow bypass passage.

In a third aspect the invention may broadly be said to consist in a system for providing gases to a patient for therapeutic purposes, said system including a blower unit, a humidifier unit fluidically connected to said blower unit, a user interface, and a conduit, one end of said conduit fluidically connected to an outlet of said humidifier, the other end of said conduit fluidically connected to said user interface so that in use gases from said humidifier can pass along said conduit and into said interface, said user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent one of said nares of said patient, each one of said pair of nasal pillows divided into three separate passages, each of said passages sealed from the other passages at least within said pillows, the first one of said passages configured to act in use as a gases delivery passageway and connected to said main body so that in use gases from said conduit can pass along said first passage to said patient, the second one of said passages configured to act as a pressure measurement duct in use, and the third one of said passages open to atmosphere and adapted to act as a high-flow bypass passage.

In a fourth aspect the invention may broadly be said to consist in a system for providing gases to a patient for therapeutic purposes, said system including a blower unit, a humidifier unit fluidically connected to said blower unit, a user interface, and a conduit, one end of said conduit fluidically connected to an outlet of said humidifier, the other end of said conduit fluidically connected to said user interface so that in use gases from said humidifier can pass along said conduit and into said interface, said user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent nare of said patient, each one of said pair of nasal pillows divided into two separate passages, each of said passages in each pillow sealed from the other, the first one of said passages configured as a gases delivery passageway and connected to said main body so that in use gases from said gases stream pass along said first passage to said patient, the second one of said passages open to atmosphere and adapted to act as a high-flow bypass passage.

In a fifth aspect the invention may broadly be said to consist in a method of reducing the likelihood of an apnoea event or a snoring event in a user who is receiving gases from a system adapted to provide a pressurised gases stream to a user through a high-flow user interface, said system including control circuitry that includes a memory component, said method comprising the steps of:

a) measuring the flow rate through the system in real time, b) increasing an output parameter provided by said system if said flow rate flattens.

In a sixth aspect the invention may broadly be said to consist in a method of providing a gases flow to a user via a high-bypass flow nasal user interface of known geometry and dimensions, said user interface in use forming part of a system which provides gases at a pressure above atmospheric to a user, said system including a blower unit and control circuitry which includes control algorithms, said method comprising the steps of:

a) using said control algorithms to calculate the resistance to flow based on said known geometry and dimensions of said nasal interface, b) using said control algorithms to calculate the bypass flow rate for a range of pressure and flow values suitable for providing gases therapy to said user, c) using said control algorithms to set an initial value of either pressure or flow to be provided by said blower unit, based on said calculations in steps 1) and 2).

In a seventh aspect the invention may broadly be said to consist in a method of real time in-use adjustment of the pressure provided to a user by a gases supply system of the type which includes a blower unit having control circuitry which includes control algorithms, and a variable speed fan unit controlled by said control circuitry, in use said gases supply system supplying gases for therapeutic purposes at a pressure above atmospheric to a user via a user interface, said user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent one of said nares of said patient, each one of said pair of nasal pillows divided into three separate passages, each of said passages sealed from the other passages at least within said pillows, the first one of said passages configured to act in use as a gases delivery passageway and connected to said main body so that in use gases from said conduit can pass along said first passage to said patient, the second one of said passages configured to act as a pressure measurement duct in use, and the third one of said passages open to atmosphere and adapted to act as a high-flow bypass passage, and further having known geometry and dimensions, said method comprising the steps of:

a. setting an initial value of either pressure or flow to be provided by said blower, and providing a stream of gases from said blower to said user via said user interface, b. measuring the differential pressure between atmospheric pressure and the pressure at said interface in use and relaying data relating to said measured differential pressure value to said control circuitry, c. measuring the flow rate provided by said blower and relaying data relating to said measured flow rate value to said control circuitry, d. using said control algorithms to make a calculation relating to the actual pressure in said patients airway by using said pressure data, said flow data and said known geometry and dimensions of said interface, e. comparing said calculated actual pressure value to said initial value, f. using said control circuitry to send control signals in real time to said fan to increase ox decrease speed so that the difference between said calculated actual pressure value and said initial value is decreased.

Preferably in said method or methods said initial value is a pressure value, and said calculated actual pressure value is directly compared to said initial pressure value.

Alternatively in said method or methods said initial value is a flow value and said method or methods includes the step of using said control algorithms to convert said initial flow value to an equivalent pressure value so that said calculated actual pressure value can be compared to said initial flow value.

Preferably said methods can be applied to a user who is receiving gases through a user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent one of said nares of said patient, each one of said pair of nasal pillows divided into three separate passages, each of said passages sealed from the other passages at least within said pillows, the first one of said passages configured to act in use as a gases delivery passageway and connected to said main body so that in use gases from said conduit can pass along said first passage to said patient, the second one of said passages configured to act as a pressure measurement duct in use, and the third one of said passages open to atmosphere and adapted to act as a high-flow bypass passage.

Preferably said methods can be applied to a user who is receiving gases through a user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent nare of said patient, each one of said pair of nasal pillows divided into two separate passages, each of said passages in each pillow sealed from the other, the first one of said passages configured as a gases delivery passageway and connected to said main body so that in use gases from said gases stream pass along said first passage to said patient, the second one of said passages open to atmosphere and adapted to act as a high-flow bypass passage.

Preferably in said methods said output parameter is pressure.

Alternatively in said methods said output parameter is flow.

Preferably said methods can be applied to a user who is receiving gases through a nasal cannula.

Alternatively said methods can be applied to a user who is receiving gases through a user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent one of said nares of said patient, each one of said pair of nasal pillows divided into three separate passages, each of said passages sealed from the other passages at least within said pillows, the first one of said passages configured to act in use as a gases delivery passageway and connected to said main body so that in use gases from said conduit can pass along said first passage to said patient, the second one of said passages configured to act as a pressure measurement duct in use, and the third one of said passages open to atmosphere and adapted to act as a high-flow bypass passage.

Alternatively said methods can be applied to a user who is receiving gases through a user interface comprising;

a substantially hollow main body, adapted for attachment to one end of said conduit so that in use said gases stream from said conduit can enter said main body, a pair of nasal pillows, fluidically connected to said main body, a portion of the outer surface of each one of said pillows adapted so that in use each of said pillows can substantially seal against the equivalent nare of said patient, each one of said pair of nasal pillows divided into two separate passages, each of said passages in each pillow sealed from the other, the first one of said passages configured as a gases delivery passageway and connected to said main body so that in use gases from said gases stream pass along said first passage to said patient, the second one of said passages open to atmosphere and adapted to act as a high-flow bypass passage.

Preferably said third one of said passages open to atmosphere immediately adjacent to said nare Preferably said main body is internally divided, so that said gases stream divides into two substantially equal portions which pass out of said main body, one portion to each to each of said pillows.

Preferably said main body is further internally divided so that each of said second ones of said passages merge within said main body into a single main body pressure measurement duct, said main body pressure measurement duct sealed from said gases stream entering said main body from said conduit.

Preferably said patient interface further includes an interface pressure sensor, said main body pressure measurement duct fluidically connected to said pressure measurement sensor in use.

Alternatively said patient interface further includes a pressure sensor and a tube, said pressure sensor located remotely from said main body and said pillows and connected to said main body pressure measuring duct by said tube.

Preferably said interface pressure sensor is a standard pressure sensor.

Alternatively said interface pressure sensor is a single differential pressure sensor.

Preferably said user interface geometry and dimensions are chosen to provide a fixed resistance to flow such that when a differential pressure of 10 cmH$_2$O is provided to said interface in use, the flow rate through said high-flow bypass passage is substantially between 50 to 70 Liters per minute.

Preferably each of said nasal pillows are formed from a soft rubber material.

BRIEF DESCRIPTION OF THE DRAWINGS

A preferred form of the present invention will now be described with reference to the accompanying drawings.

DETAILED DESCRIPTION OF THE PREFERRED EMBODIMENTS

Figure 1:
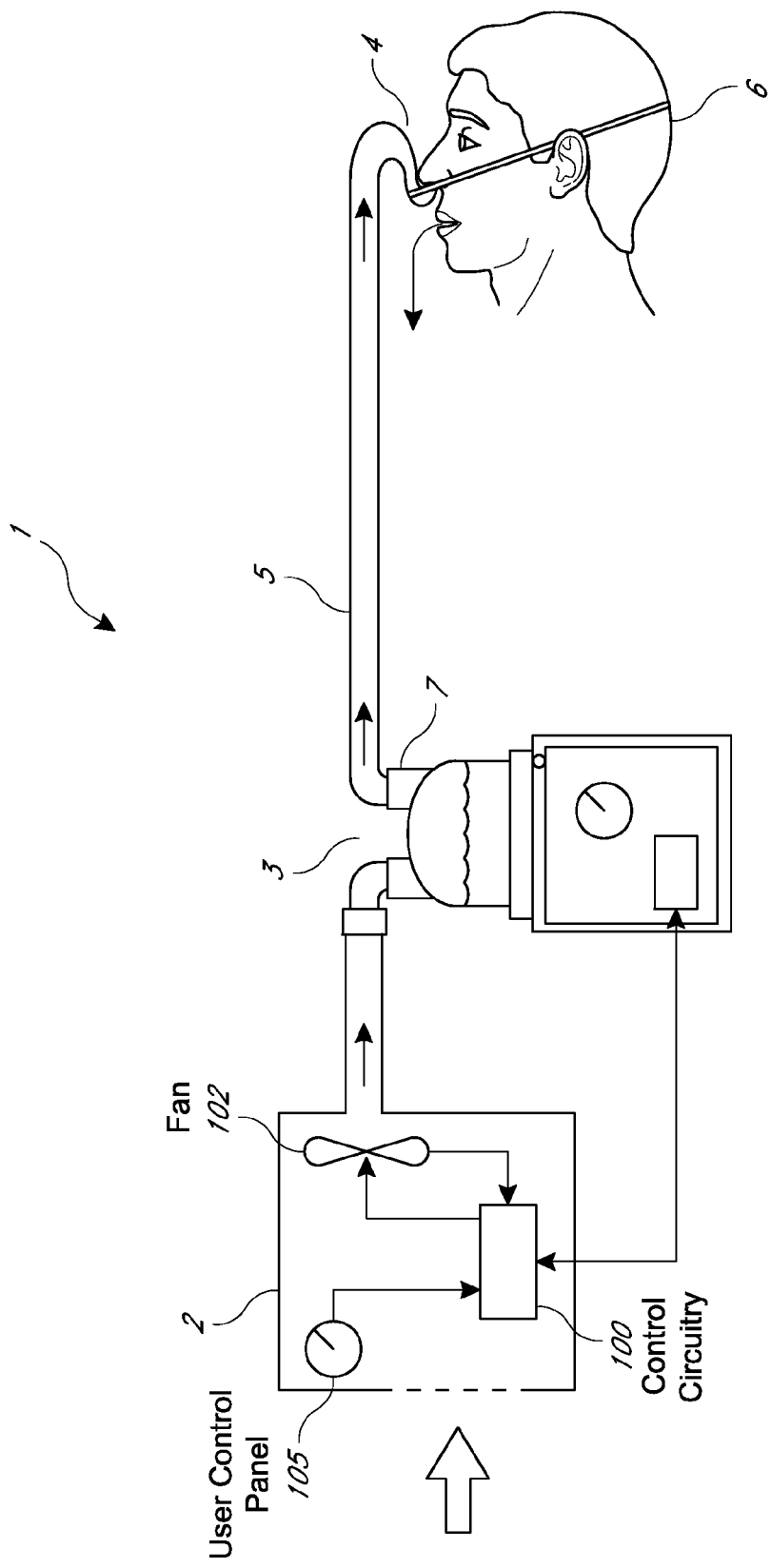
FIG. 1 shows a schematic view of a user receiving humidified air from a modular blower/humidifier system of a known, prior art, type.

The present invention will be described with reference to a gases supply system 1 comprising four main parts: a blower unit 2, a humidifier unit 3 connected to the blower unit 2, a patient interface 4, and a conduit 5 connecting the patient interface 4 with the humidifier unit 3. In the example system shown in FIG. 1, the humidifier unit 3 is separate to the blower unit 2 (which can also be referred to as a respirator unit or gases supply unit). Systems of this type where the humidifier unit 3 and the blower unit 2 are separate items are usually referred to as modular systems. Systems where the blower unit and the humidifier unit are rigidly connected can be referred to as integrated units. However, it should be noted that the invention is equally applicable to either a modular system (a system where the humidifier unit 3 and the blower unit 2 are separate and connected by a flexible conduit or similar), or an integrated system.

It is not necessary to describe all the details of the structure of the system 1 in order to fully describe the present invention. However, it should be noted that the primary purpose of the system 1 is to provide a stream of gases to a user 6 at a pressure above atmospheric pressure, and it is preferred that these gases are heated and humidified. The gases stream is provided to a user for therapeutic purposes—e.g. for treating sleep apnoea, snoring or similar.

As outlined above, the blower unit 2 provides a stream of air to the humidifier unit 3, where it is heated and humidified. Ideally, the patient receives gas at a temperature of substantially 34 degrees Celsius and a humidity of 95% (although the most acceptable range is between 30-37 degrees Celsius and 85-100% humidity, and it should be noted that in certain circumstances gases can be provided which fall outside this range of temperature and humidity). The patient or user 6 receives the heated, humidified gases via a user interface 4, which is fluidically connected to one end of flexible conduit 5, the other end of which is fluidically connected to the outlet 7 of the humidifier 3, so that gases can pass along the conduit 5 to the user interface 4. If required, the conduit 5 can be heated to maintain the gases temperature and humidity levels after the gases leave the humidifier.

Figure 9:
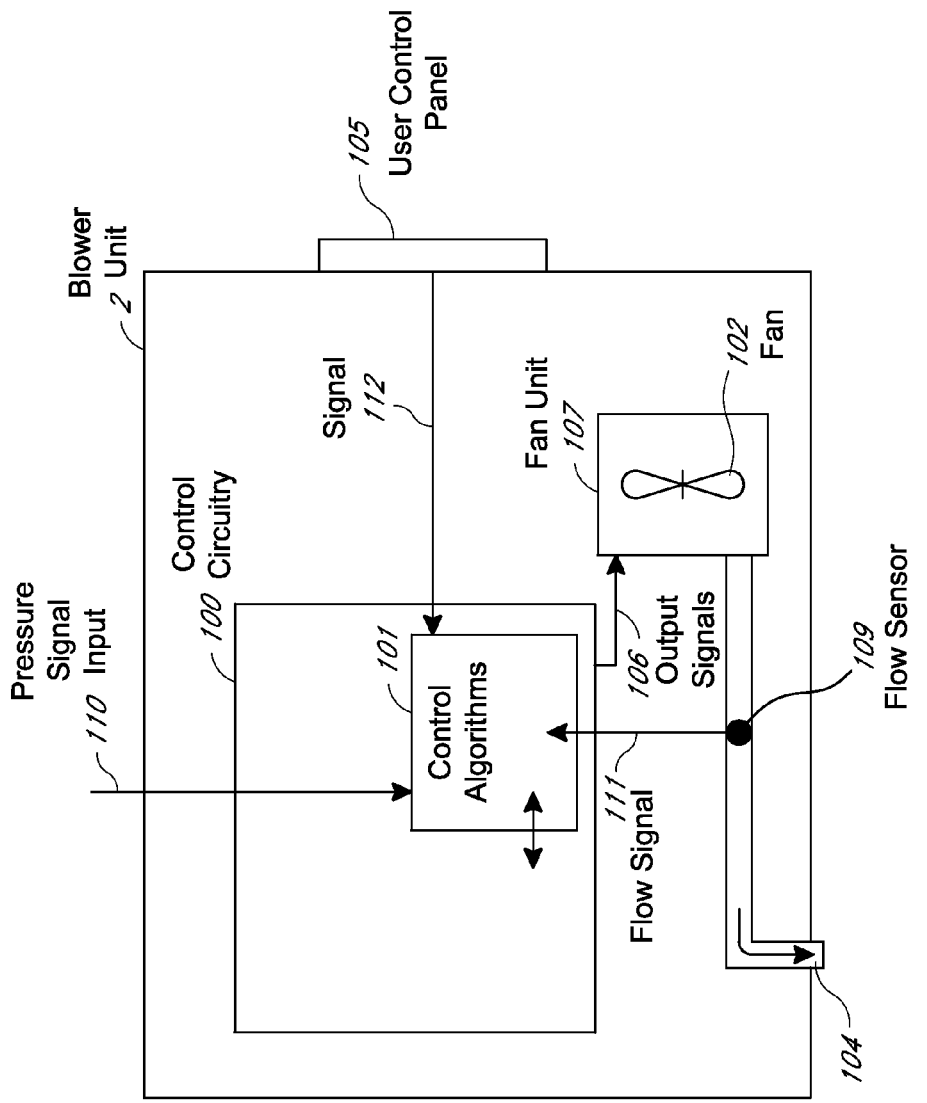
FIG. 9 shows a schematic view of a blower unit that forms part of the gases delivery system, showing interconnections between control circuitry located inside the blower unit, control algorithms contained within the control circuitry, inputs from sensors associated with the gases delivery system, and inputs from a user control panel, and outputs to a fan unit located inside said blower unit in response to signals sent from the control circuitry, the signals calculated using outputs from the control algorithms.

In use, the blower unit 2 is initially set to a user-specified pressure or flow level—an initial value. A schematic layout of the blower unit 2 is shown in FIG. 9, which shows a schematic view of a blower unit that forms part of the gases delivery system. Interconnections representative of data signals are shown between control circuitry 100 which is located inside the blower unit, control algorithms 101 contained within the control circuitry, a pressure signal input 110 from a pressure sensor or sensors associated with the gases delivery system, inputs from a user control panel 105, and output signals 106 to a fan unit 107 located inside the blower unit 2 are also shown. The output signals 106 are sent from the control circuitry 100 and are calculated using outputs from the control algorithms 101. The control circuitry 100 adjusts the speed of the internal fan or impeller 102 within the fan unit 107 to provide the user-requested pressure or flow level, shown as output 104. In the preferred form, the output 104 will pass into the humidifier unit 3. The system 1 also includes various sensors which measure operating parameters of the system as follows:

The static atmospheric pressure may be measured—e.g. by means of a static pressure sensor located at or on the blower unit 2. For example, the static pressure sensor can be on, in or recessed into the casing of the blower unit 2. The pressure at the interface 4 may be measured by using an interface pressure sensor 2000 located on or in the interface 4, measuring the pressure of the flow of gases provided to the interface by the blower. The two pressure measurements are sent to the control circuitry as a pressure signal input 110 as shown in FIG. 9 and compared using the control algorithms in order to find the differential pressure. Alternatively the interface pressure sensor 3000 can be a single differential pressure sensor which measures the pressure difference between the interface and atmospheric pressure directly, and which sends a pressure signal input 110.

This pressure value is the value that is set by a medical professional such as a clinician when they initially prescribe the pressure level for a patient. The medical professional may alternatively prescribe a flow rate for the patient or user.

Additionally, if desired the flow rate of the gases stream can be measured by means of a flow sensor 109 located in the blower unit 2. It is preferred that the flow sensor is placed at a position in the system where the measured flow will be reasonably constant, for example at the outlet of the fan that is enclosed within the casing of the blower unit 2, or a similar position. The flow at other locations in the system can be disrupted by the users breathing cycle and it can therefore be difficult to measure the flow rate accurately. That is, it can be difficult to measure the flow rate in a manner that allows adjustments to fan speed to be made which are of the necessary precision so that the users therapy regime is effectively altered on a breath-to-breath basis. A signal 111 corresponding to the measured flow is sent to the control circuitry.

In the preferred form as outlined above, the user interface is used as part of a system 1 for providing a pressurised gases stream to a user, which is most preferably heated and humidified. A user sets the blower unit 2 to an initial setting, which is a constant pressure setting. This initial level can be adjusted using the control panel 105 according to the users needs and signal 112 is sent to the control circuitry indicative of the initial set value. For a constant pressure setting, the flow rate delivered by the blower unit 2 may vary, depending on the breathing of the user 6. For example, the delivered flow will drop when the user 6 exhales. An ideal CPAP device delivers a constant pressure for all breathing flow rates. However, in practice a constant pressure for all flow rates is practically unachievable. Therefore, for any given user-set pressure, the actual pressure delivered by the blower unit 2 will vary as a user inhales and exhales, and as the speed of the fan is altered to alter the flow rate.

The preferred form of fan unit is speed adjustable, to provide a range of differential pressures. The usual (most common) level which is used by the majority of users is in the region of 20 $cmH_2O$. However, differential pressures of between approximately 4 $cmH_2O$ up to 60 $cmH_2O$ can be used in therapy regimes.

The preferred embodiments of the user-interfaces of the present invention relate to two types of user interface: a sealed interface 4 and an unsealed interface (not shown). These are described below.

Sealed User Interface with a High Bypass Flow

Figure 2A:
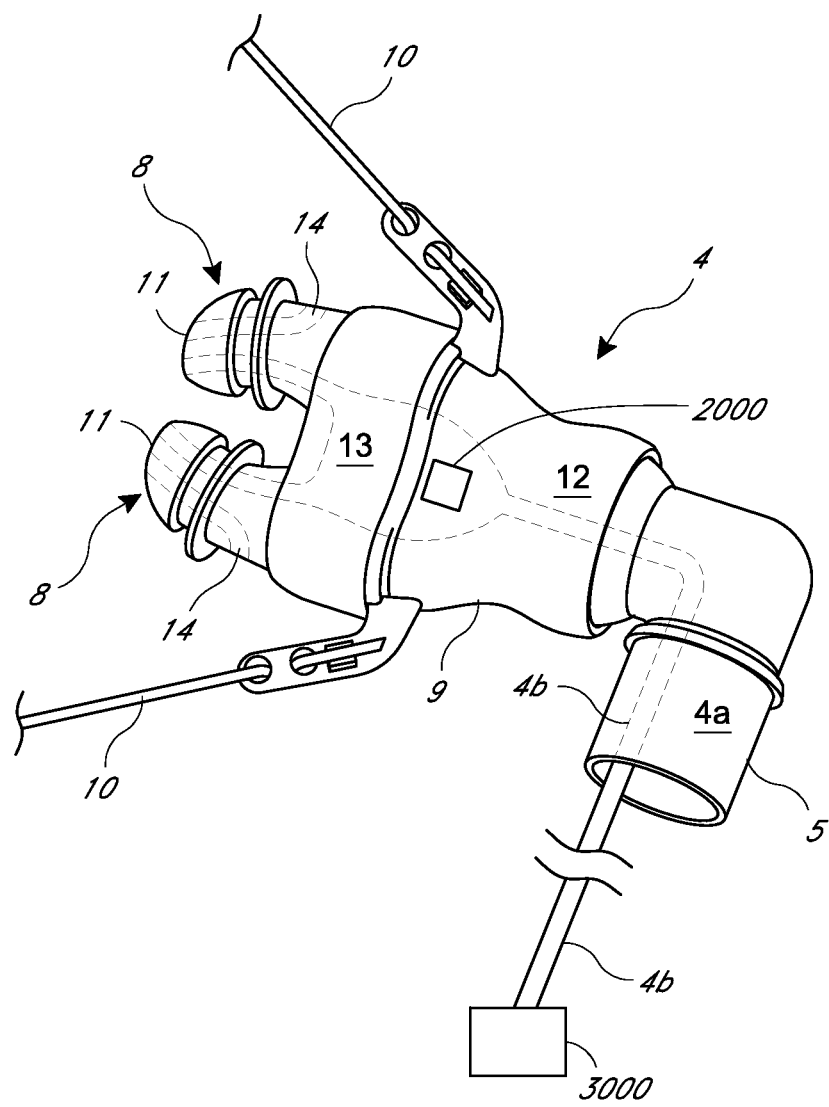
FIG. 2a shows a perspective view of the preferred embodiment of the interface of the present invention, the interface consisting of a pair of nasal pillows attached to a main body, the main body having an attachment for headstraps and an attachment adapted to receive a gases conduit.
Figure 2B:
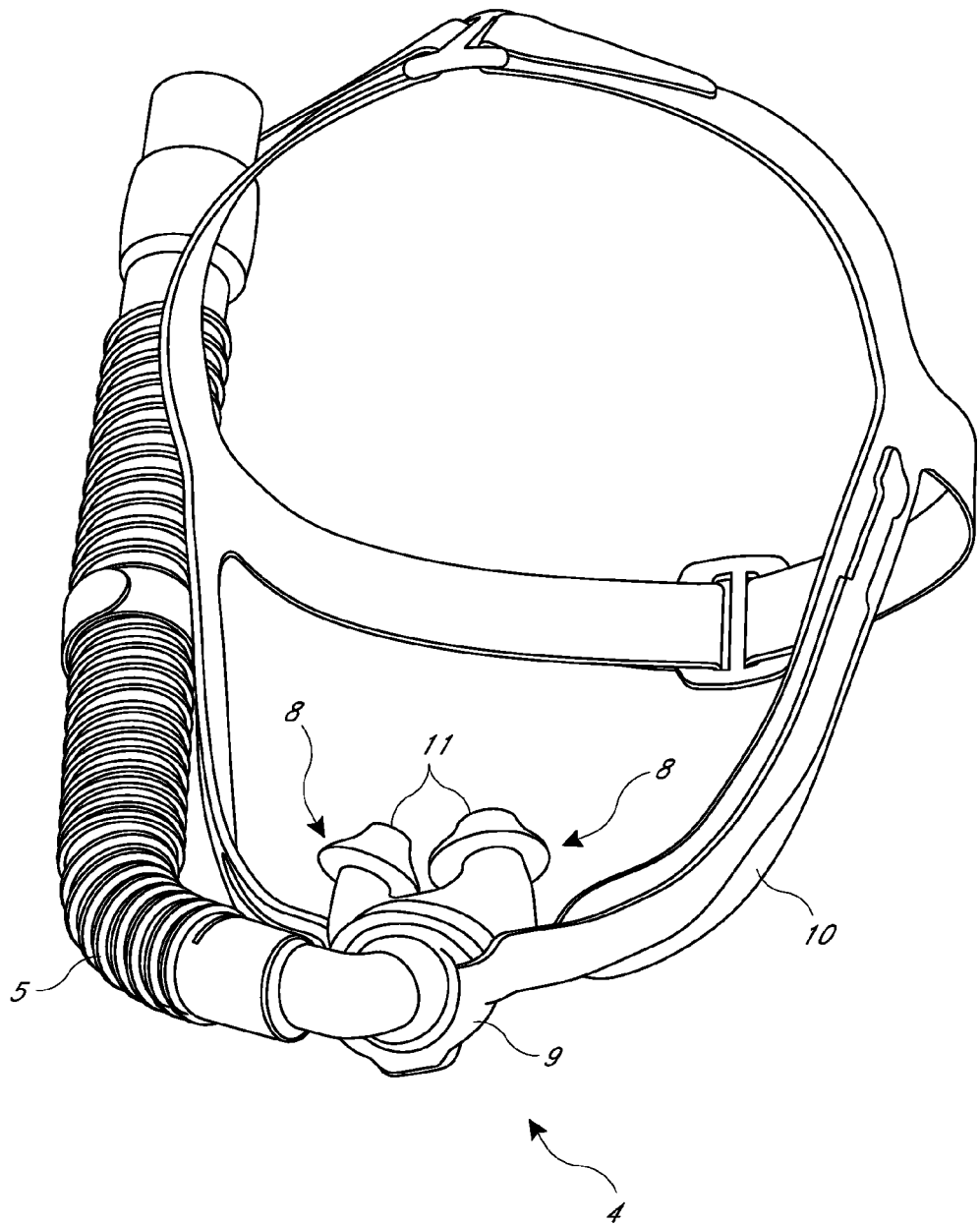
FIG. 2b shows a perspective view of the preferred embodiment of the interface of the present invention attached to a headgear, with a conduit attached to provide a pressurised gases stream to the main body of the interface.

The preferred form of sealed user interface 4 is shown in FIGS. 2a and 2b. The user interface 4 is intended to seal against the nares of the user 6, and comprises a set or pair of nasal pillows 8, mounted on a housing or main body portion 9 so that gases can freely pass between the main body 9 and the nasal pillows 8—they are fluidically connected. It should be noted that within the context of this specification, 'nasal pillows' refers to an interface which seals against the nares of a user, and 'nasal cannula' refers to an interface that includes prongs which do not seal against the users nares. In the preferred form, the main body portion 9 is connected to a headgear assembly 10 which in use holds the interface 4 in position on the user 6. One end—the user end—of the conduit 5 is fluidically connected to the body portion so as to provide a stream of heated humidified gases to each of the nasal pillows 8, with the other end connected to the outlet of the humidifier unit 3. This enables a stream of heated humidified gases to be provided in use from the humidifier unit 3 to a user via their nose. The nasal pillows 8 include, or are integrally formed as, a seal or sealing mechanism 11 which seals around or against the inside of the nares of the user 6 in use. The seal is a soft rubber or silicone flange 11 or similar. The internal cross-sectional structure of the interface 4 and the pillows 8 is described in detail below with reference to FIGS. 3a, 3b and 3c.

Figure 3A:
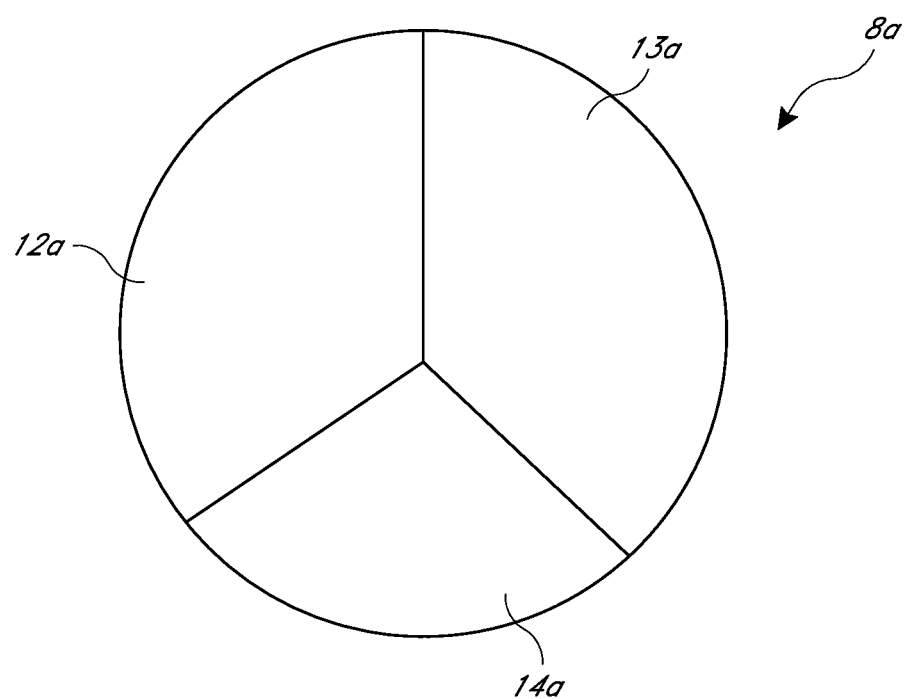
FIGS. 3a, b and c show schematic cross-sections of three different preferred forms of the nasal pillows of the present invention.
Figure 3B:
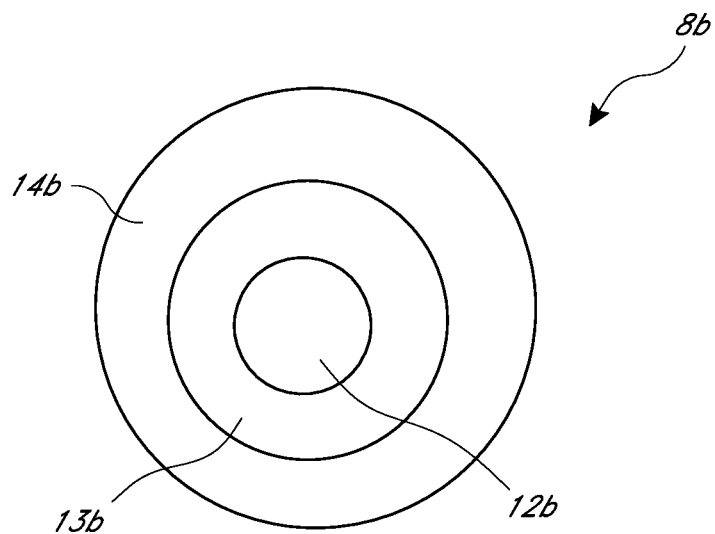
Figure 3C:
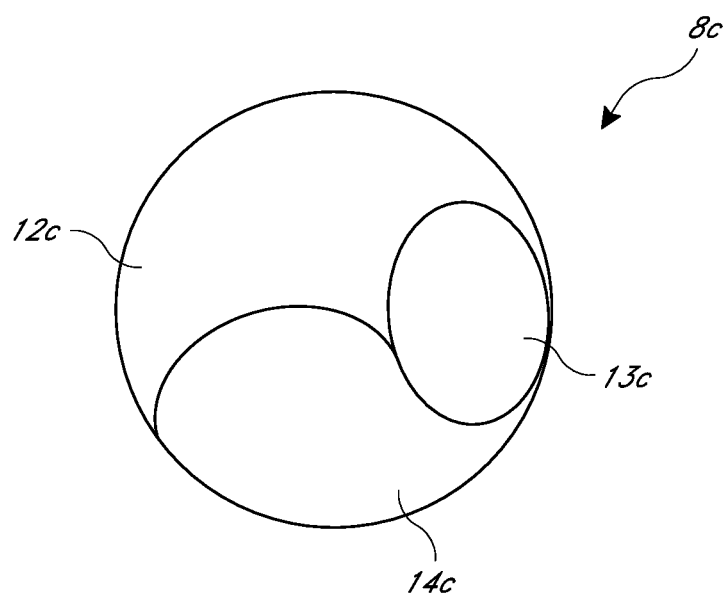

FIGS. 3a, 3b and 3c show a cross-section of three preferred forms of one of the pair of nasal pillows 8a, 8b, 8c (i.e. the figures show either the left one or the right one of the pair of pillows—each one for each nostril is identical to the other). As can be seen, for each of the preferred forms, the cross-section is divided into three separate parts, portions or passages. In FIG. 3a, these are shown as three different sectors or sections of the circle—'slices'. In FIG. 3b, three concentric circles are shown, representing a concentric conduit structure. The outer surface or edge of the pillows 8b seals against the nares of the user. FIG. 3c shows the cross-sectional area of the circle divided into three portions asymmetrically. It should be noted that all of the examples shown are schematic representations and are not necessarily indicative of the actual geometry of the nasal pillows 8a, 8b, 8c. Each of the passages is sealed from the others so that there is no intermingling of the gases when they are in the passages.

Figure 6:
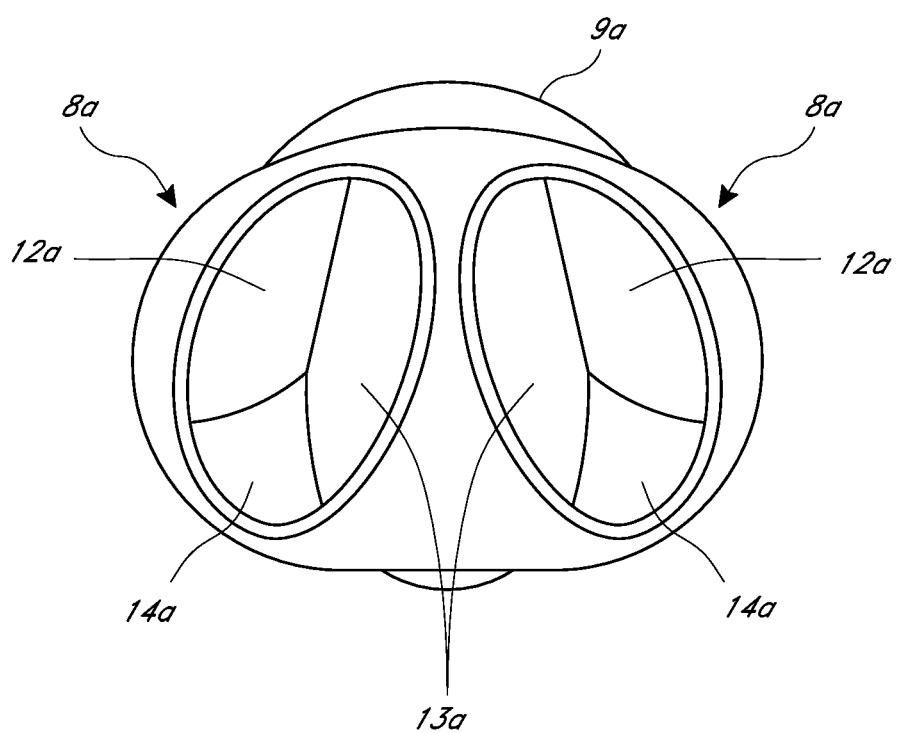
FIG. 6 shows a user end view of the nasal pillows of FIG. 2, having a cross-section as shown in FIG. 3c.

FIG. 6 shows a user-end view of the interface 4, with the nasal pillows 8a configured so that each is divided into three 'slices' as described above and shown in FIG. 3a.

The operating principle in each case is the same. Gases are delivered from the main body 9 through a first (or delivery) one of the three passages or sections (e.g. one of the 'slices' or one of the concentric circle sections). For example, either section 12a in FIG. 3a, section 12b in FIG. 3b, or section 12c in FIG. 3c. Pressure is measured through a second one of the three sections or passages—e.g. section 13a in FIG. 3a, or section 13b in FIG. 3b, or section 13c in FIG. 3c. The third section or passage 14a, 14b or 14c is adapted to allow controlled high-volume bypass flow or venting. That is, in the most preferred form a stream of heated and humidified gases are delivered to the upper airway or nasal cavity of a user 6 via the delivery section 12a, 12b or 12c. When a user 6 is inhaling, the majority of these delivered gases will be drawn into the users lungs. As the user 6 exhales, the preferred construction allows the majority of the gases to immediately vent to atmosphere via the vent 14a, 14b or 14c, which are located substantially immediately adjacent to the nares of the user (e.g. in use ideally not more than 5-6 mm from the patients nares, and very preferably less than 10 mm-15 mm. When the word 'immediately' is used in this specification, it should be taken to mean less than 10-15 mm). Alternative constructions are possible, where the vents are located at a distance greater than this from the nare of the user. The construction should not be limited to 'immediate' venting unless specifically stated.

In the preferred form, the delivery conduit 5 is divided into two separate portions along its length. The first portion 4a forms part of the delivery section—i.e. ending at delivery section 12a or 12b, and transports heated humidified gases from the humidifier. The second portion 4b is used to measure the pressure and runs between the blower unit 2 and the pressure measurement section 13a, 13b, 13c.

It should also be noted that in the preferred form, the nasal pillows 8 are adapted so that the vent section(s) 14a, b or c vent to atmosphere immediately adjacent to the nares of the patient. The two remaining sections (12 and 13) divide within the main body portion 9 so that gases are provided into the upper airway via one section 12, which branches within the body 9 so as to provide pressure to each pillow 8, and pressure is measured via the other section 13, which also divides or branches within the body 9. That is, the main body 9 is internally divided.

For a normal or prior art nasal cannula, with thin nasal inlet sections substantially smaller than the internal cross-sectional area of the user's nostrils, any venting or similar around the inlet sections is uncontrolled leaking. The exact nasal geometry and dimensions are unknown, and therefore the proportion of gases venting to atmosphere around the outlets of the unsealed nasal cannula is unknown and therefore uncontrolled.

In contrast, the proportions of a sealed, high-bypass nasal pillow interface such as the preferred embodiment described above are known from the geometry and the dimensions. The bypass venting or bypass flow can be referred to as 'controlled leaking'. Effectively, because the resistance to flow is fixed, the relationship between pressure and flow can be calculated.

Feedback and Adjustment Using a Sealed Interface with a High Bypass Flow

As has been described above, the nasal pillows 8 of the present invention allow a known amount of gas to vent or bypass at the patient interface 4. The geometry of the patient interface 4 is fixed. Uncontrolled leaking is minimised to the point where it is effectively irrelevant. The system is built so as to include a bypass path with known geometry and dimensions, which has a lower resistance by several orders of magnitude than any uncontrolled leak path around the seal 11, and also bias vent holes such as are known in the prior art. The resistance to flow of the interface 4 is fixed and therefore for any size or particular variant of the construction the resistance to flow can be calculated from the specific geometry and dimensions. As outlined above, the flow from the blower unit 2 is measured by means of a flow sensor. As the flow rate is known from the reading of the sensor, and the bypass or vent path is known, accurate real time calculation of the actual pressure in the patients upper airway or nasal cavity can be achieved by sensing the flow data and transmitting this data to control algorithms programmed into or located in the control circuitry of the blower unit 2. The control circuitry receives data input from the flow sensor and the pressure sensors (so the differential pressure can be calculated). As the resistance to flow is known from the geometry, the pressure in the upper airway or nasal cavity can be calculated using the control algorithms. Therefore, the pressure can be adjusted as necessary, by sending control signals to the fan so that the fan speed is adjusted to alter the pressure.

As outlined in the 'background of the invention' section above, high flow nasal cannula are frequently used to provide gas for treatment of illnesses including COPD, CF and OSA amongst many others. It is desirable to set a flow rate through the cannula that is sufficient to meet the patient's maximum inspiratory demand, but which does not significantly exceed that required to meet maximum inspiratory demand. By measuring or calculating the pressure at the interface exit or nares in the manner outlined above, and ensuring that this pressure is always greater than atmospheric pressure, the flow rate can be set so that it is sufficient to meet the patient's maximum inspiratory demand, but so that it does significantly exceed that required to meet maximum inspiratory demand. To ensure that the flow delivered is equal to that required to meet maximum inspiratory demand the flow can be adjusted so that minimum pressure at the nares/interface is approximately equal to atmospheric pressure.

By continuously monitoring pressure the flow rate can be adjusted over time to accommodate changes in peak inspiratory demand. This can be done manually by the user or clinician. Alternatively, this can be carried out automatically via a feedback mechanism where the pressure, flow and/or blower speed is varied at the flow generator.

With the interface design outlined here the pressure delivered is a well defined function of the flow exiting the exhaust section of the interface. Furthermore in the preferred embodiment as described above, where the interface includes a passage allowing pressure measurement at the interface or near the nares, the pressure delivered during expiration can be measured and adjusted. The can be done by adjusting the pressure, flow and/or blower speed of the flow generator. Furthermore this can be done manually or, preferably, automatically.

The arrangement described above also has the advantage that it is far easier for a patient to exhale against the incoming flow than with prior art nasal pillows where there is no flow venting directly at the interface (nasal pillows with flow venting e.g. at an elbow connector just upstream of the interface are known. It is also known to add bias vent holes in a housing that is used with nasal pillows in order to provide bias venting). As noted above, masks which include bias vent holes typically vent approximately 35 Liters per minute of exhaust flow when the pressure is around 10 cmH$_2$O above atmospheric pressure (a differential pressure of 10 cmH$_2$O).

In contrast, in a system such as the one described above, the blower unit 2 will typically provide a flow rate of between 20 Liters per minute to 60 Liters per minute (although the flow rate could also lie outside these limits). The mask pressure to produce the required flow will typically be in the range 0.5 to 15 cmH$_2$O. The resistance to flow using the arrangement described above is between two to four times less than the equivalent in conventional masks. That is, the resistance to flow of the bypass passage is such that the flow rate at a pressure of 10 cmH$_2$O will typically be 50 to 70 Liters per minute at a pressure of 10 cmH$_2$O.

It should be noted that the term 'sealed' as used in the context described above means that an effective seal is created around the nares of the patient or user 6. Clearly, due to the high bypass flow, the system is not effectively sealed against atmosphere. However, the bypass flow is controlled as the geometry of the interface is known. Therefore, other parameters can be accurately measured or calculated in order for the system 1 to be effectively controlled.

It is preferred that a sealed patient interface is used, as there are advantages in terms of patient comfort. For example: entraining of atmospheric air is minimised; the flow rate can be effectively measured; the patient interface will not tend to be pushed off the users face as the user exhales causing leaks and leading to discomfort; and the resistance to flow is two to four times less than with equivalent mask systems that include bias venting. Also, a general advantage of using nasal pillows is that all of the humidified flow at the interface is delivered into the nostril of a user. In contrast, when using e.g. a nasal mask a proportion of the flow will vent (through bias vent holes) before reaching the user interface (mask). It is also preferred for the purposes of patient comfort that the gases provided to the patient are heated and humidified. Although this is strongly preferred, it is not absolutely necessary.

A further advantage of using a design based on sealed nasal pillows with a separate isolated leak path is that the escaping gas passing through the leak path can be passed to atmosphere further from the user, reducing the perceived noise. Furthermore, because the resistance of the gas exhaust section of the pillows and geometry of the exit aperture is well defined, the noise level is reduced and consistent.

In some circumstances it can be advantageous to use a normal nasal cannula—that is, an unsealed system where the geometry is not known. The advantages are outlined below.

Feedback and Adjustment Using a Sealed or an Unsealed User Interface

Figure 4:
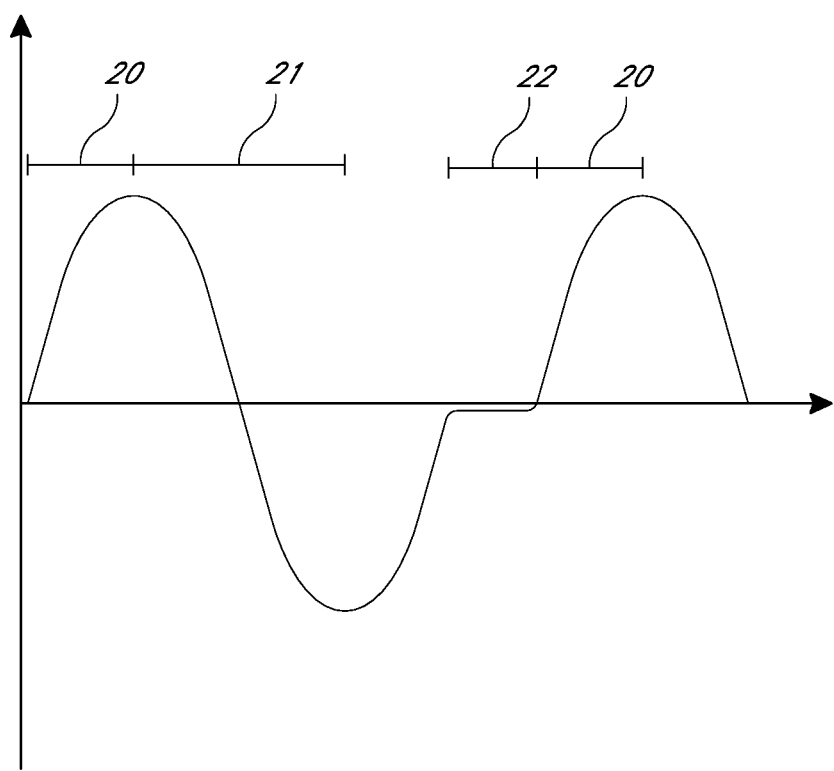
FIG. 4 shows a typical graph of flow rate (y-axis) vs time (x-axis) for a healthy user inhaling and exhaling.
Figure 5:
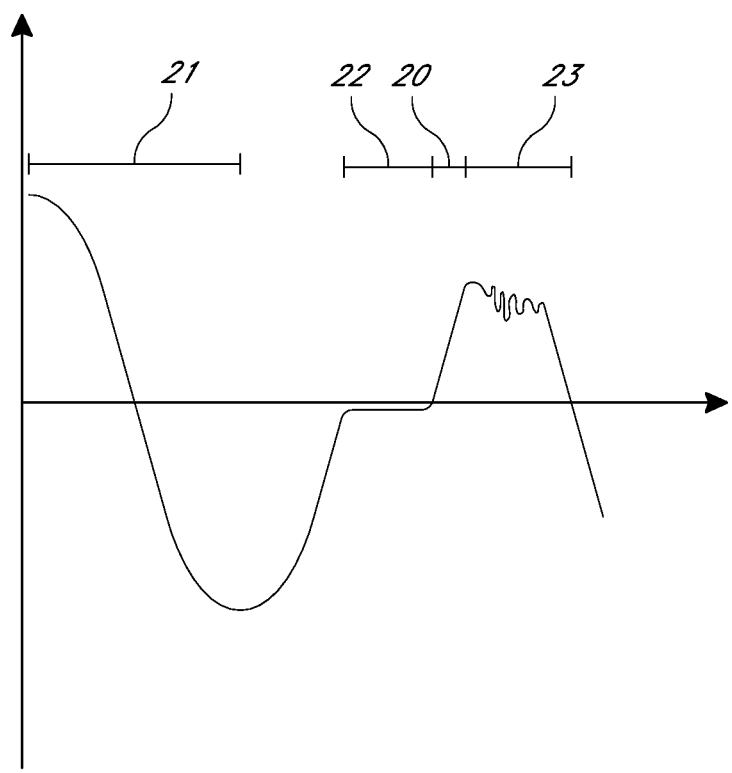
FIG. 5 shows a typical graph of flow rate (y-axis) vs time (x-axis) for a user who may require breathing assistance, with abnormalities in their breathing cycle.

As can be seen from a comparison of the graphs in FIGS. 4 and 5, there is a marked difference between normal breathing and breathing characterized by a partial airway obstruction, all in low frequencies. The present application exploits this difference to control the delivery of therapeutic gas. When the flow rate is measured for a breathing system that is used with a high-flow rate user interface, there is an improvement in the detection of abnormal flow (e.g. a flattening of the inhalation curve, potentially in combination with a lengthening of the inhalation curve, and also potentially in combination with the inhalation curve becoming jagged or spiky).

A typical graph of flow vs time for a healthy user inhaling and exhaling is shown in FIG. 4. The inhalation portion of the cycle is shown as inhalation portion 20. The user then exhales as shown in portion 21, and there is then a pause as shown in section 22 before the cycle starts again. As can be seen, for a healthy user, the curve is generally smooth and apart from the 'pause' section at 22 follows a sinusoidal pattern.

A typical graph of flow vs time for a user who may require breathing assistance is shown in FIG. 5. A potential abnormality is shown in the inhalation portion of the curve at 23, where in contrast to the curve for the healthy user, the inhalation curve flattens. Studies have shown that as well as flattening, the curve may also become irregular—jagged or ridged indicating some form of upper airway resistance. In abnormal sleep breathing patterns of this type, the curve will always flatten to some degree. It may also lengthen as well.

By measuring the flow rate through the system in real time, the pressure can be adjusted when the onset of an abnormal sleep breathing pattern is detected. Measurement of the flow rate with time can be carried out when the user is using a sealed interface such as interface 4 that includes nasal pillows 8 as described above, or when the user is receiving gases from an unsealed system—for example a normal nasal cannula 104. The control circuitry of the blower unit 2 can be adapted to include algorithms which increase the fan speed when an abnormality is detected, so that the pressure provided to a user is increased and airway patency is maintained.

As outlined above, another advantage of using a design based on sealed nasal pillows with a separate isolated leak path is that the escaping gas passing through the leak path can be passed to atmosphere further from the user, reducing the perceived noise. Furthermore, because the resistance of the gas exhaust section of the pillows and geometry of the exit aperture is well defined, the noise level is reduced and consistent.

Sealed High Bypass Nasal Gases Delivery System with No Adjustment

What has been described above is a system where the structure of the gases delivery interface allows pressure measurements to be made at the interface to allow adjustment of the gases pressure or the gases flow provided to a user, with the adjustment taking place in real time.

It is also possible to use a high-bypass system with known geometry which does not include pressure or flow adjustment.

In a system of this type the structure of the user interface is externally very similar to that shown in FIGS. 2a and 2b. However, there is no need for an internal pressure measurement duct. Therefore in cross-section, each of the pillows can be divided into two portions or passages instead of three.

Figure 7C:
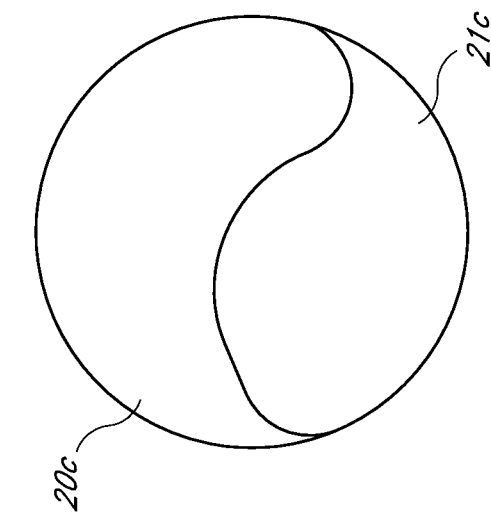
FIGS. 7a, 7b and 7c show schematic cross-sections of a second preferred form of the nasal pillows of the present invention, with two separate passages passing through the nasal pillows.
Figure 7B:
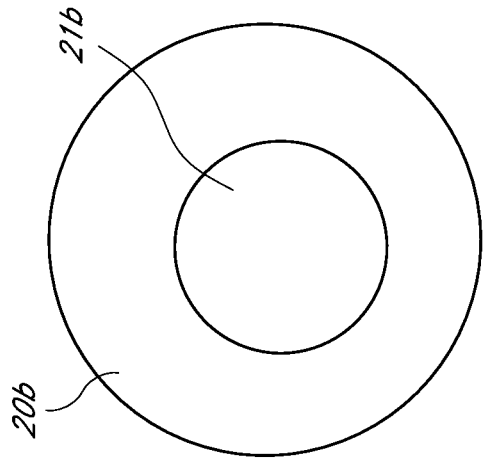
Figure 7A:
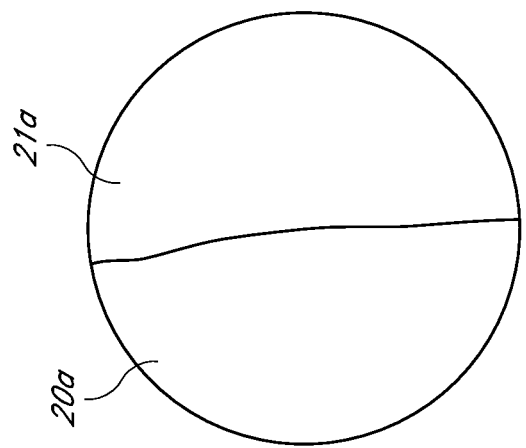
Figure 8:
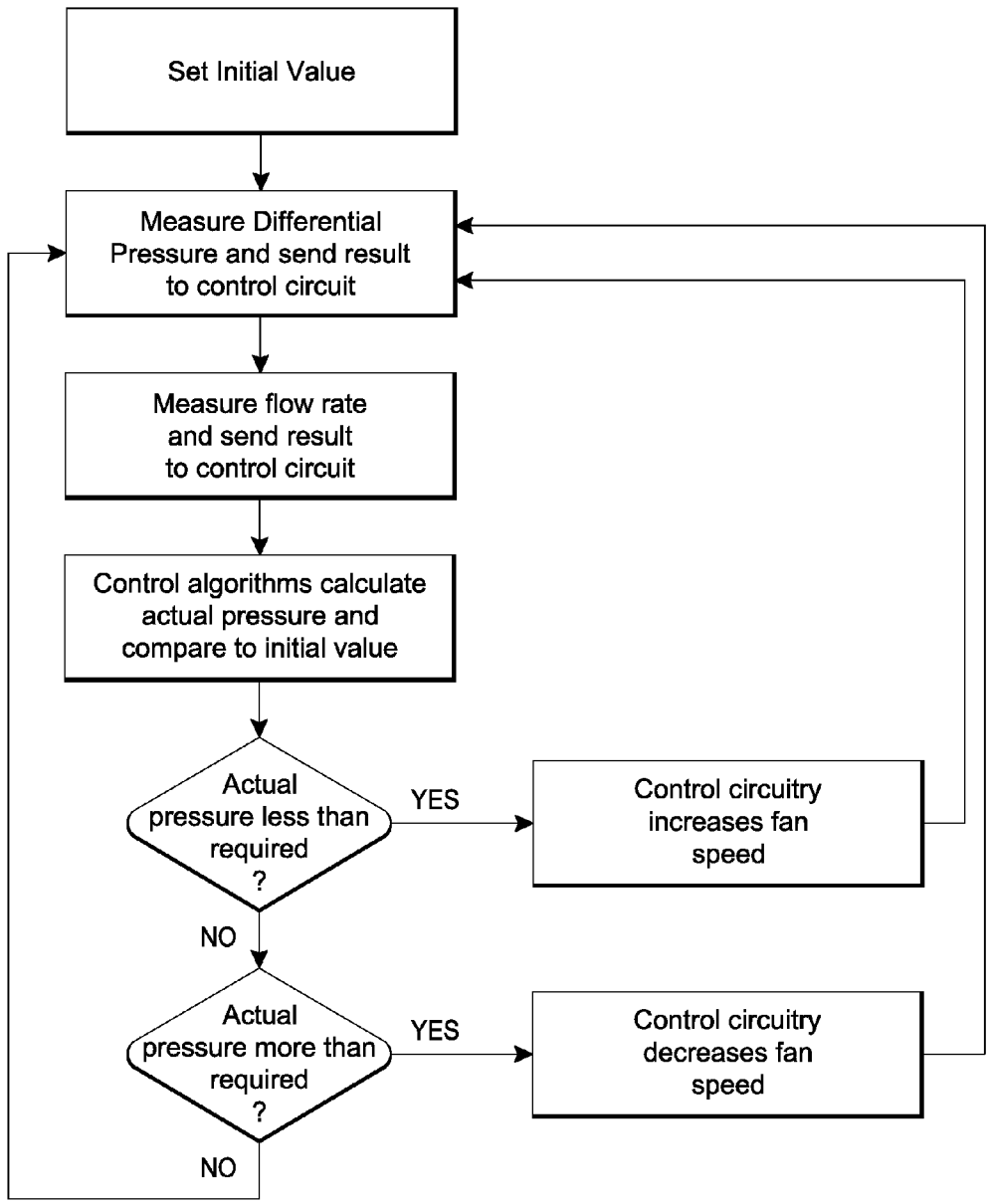
FIG. 8 shows a flow chart of the feedback process by which the characteristics of the gases stream delivered to a user may be adjusted in use in real time.

Preferred schematic cross-sections of this alternative form are shown in FIGS. 7a, 7b and 7c. In use, the gases are delivered into the nares of a user though the gases delivery passage 20a, 20b or 20c. The high bypass flow passage—either 21a, 21b, or 21c is immediately adjacent to the nares of a user, in a similar fashion to that described previously.

As the geometry of the nasal pillows are known, the resistance to flow can be calculated for any given size and geometry of user interface for the range of flow and pressures that will be used. Therefore, it is easier to calculate (and therefore set) an initial value of flow or pressure (or an in-use value to which the flow or pressure will ramp up to). There are fewer unknown variables to take into consideration—the geometry and dimensions are known, the flow rate or pressure rate is known, and the bypass flow rate can be calculated from the known geometry/dimensions, the known resistance to flow and the known initial setting of pressure or flow. A system of this type requires less in the way of initial and on-going adjustment for any given user. Also, a larger proportion of users will be able to adapt to gases therapy regimes in less time than would otherwise be the case.

Also, as has been outlined above, a design based on sealed nasal pillows with a separate isolated leak path has the advantage that the escaping gas passing through the leak path can be passed to atmosphere further from the user, reducing the perceived noise. Furthermore, because the resistance of the gas exhaust section of the pillows and geometry of the exit aperture is well defined, the noise level is reduced and consistent.

We claim:

1. A user interface for use as part of a system for providing gases to a patient for therapeutic purposes, said system comprising a gases supply conduit which in use provides a gases stream, said patient having nares, said user interface comprising;
    a substantially hollow main body adapted for attachment to one end of the gases supply conduit so that in use the gases stream from the gases supply conduit can enter said main body,
    a pair of nasal pillows fluidically connected to said main body, a portion of an outer-surface of each one of said pillows having a sealing mechanism adapted so that in use each of said pillows can seal against the corresponding nare of said patient,
    each one of said pair of nasal pillows having a divider extending longitudinally through and dividing the nasal pillow into three separate passages, each of said three separate passages sealed from the other passages at least within said pillows, a first one of said three separate passages configured to act in use as a gases delivery passageway and connected to said main body so that in use the gases stream from the gases supply conduit can pass along said first passage to the patient, a second one of said three separate passages configured to act as a pressure measurement duct in use, and a third one of said three separate passages open to atmosphere and adapted to act as a high-flow bypass passage.

2. A user interface as claimed in claim 1 wherein said main body is internally divided so that the gases stream divides into two substantially equal portions which pass out of said main body, one portion to each of said pillows.

3. A user interface as claimed in claim 2 wherein said main body is further internally divided so that said main body further comprises a main body pressure measurement duct sealed from the gases stream entering said main body from the gases supply conduit, and said second one of said three separate passages of each one of said pair of nasal pillows configured to merge within said main body into said main body pressure measurement duct.

4. A user interface as claimed in claim 3 further including an interface pressure sensor, said main body pressure measurement duct fluidically connected to said interface pressure sensor in use.

5. A user interface as claimed in claim 4 wherein said interface pressure sensor is a standard pressure sensor.

6. A user interface as claimed in claim 4 wherein said interface pressure sensor is a single differential pressure sensor.

7. A user interface as claimed in claim 4 wherein said interface pressure sensor is a standard pressure sensor.

8. A user interface as claimed in claim 4 wherein said interface pressure sensor is a single differential pressure sensor.

9. A user interface as claimed claim 3 wherein further comprising a pressure sensor and a tube, said pressure sensor located remotely from said main body and said pillows and connected to said main body pressure measuring duct by said tube.

10. A user interface as claimed in claim 1 wherein geometry and dimensions of said user interface are chosen to provide a fixed resistance to flow such that when a differential pressure of 10 cm $H_2O$ is provided to said interface in use, a flow rate through said high-flow bypass passage is substantially between 50 to 70 Liters per minute.

11. A user interface as claimed in claim 1 wherein each of said nasal pillows is formed from a soft rubber material.

12. A user interface as claimed in claim 1 wherein each of said third passages is adapted to vent to atmosphere immediately adjacent to the corresponding nare.

13. A user interface as claimed in claim 1 wherein only said third passage of said three separate passages is adapted to vent to atmosphere immediately adjacent to the corresponding nare.

14. A user interface for use as part of a system for providing gases to a patient for therapeutic purposes, the system comprising a gases supply conduit which in use provides a gases stream, the patient having nares, said user interface comprising:
    a substantially hollow main body adapted for attachment to one end of the gases supply conduit so that in use the gases stream from the gases supply conduit can enter said main body,
    a pair of nasal pillows fluidically connected to said main body, a portion of an outer surface of each one of said pillows having a soft rubber flange adapted so that in use each of said pillows can seal against a corresponding nare of the patient,
    each one of said pair of nasal pillows having a separator to separate the nasal pillow into three separate passages, each of said three separate passages in each pillow sealed from the other, a first one of said three separate passages configured as a gases delivery passageway and connected to said main body so that in use gases from the gases stream pass along said first passage to the patient, a second one of said three separate passages configured to act as a pressure measurement duct in use, and a third one of said three separate passages open to atmosphere and adapted to act as a high-flow bypass passage.

15. A user interface as claimed in claim 14 wherein said main body is internally divided so that the gases stream from the gases supply conduit divides into two substantially equal portions on entering said main body, each said substantially equal portion passing out of said main body into each of said pillows.

16. A user interface as claimed in claim 14 wherein geometry and dimensions of said user interface are chosen so that a flow rate at a pressure of 10 $cmH_2O$ will lie substantially in a range of 50 to 70 Liters per minute when a differential pressure of 10 $cmH_2O$ is provided to said interface in use, so that a resistance to flow of the bypass passage is such that the flow rate at a pressure of 10 $cmH_2O$ will typically be 50 to 70 Liters per minute at a pressure of 10 $cmH_2O$.

17. A user interface as claimed in claim 14 wherein each of said nasal pillows is formed from a soft rubber material.

18. A user interface as claimed in claim 14 wherein said second one of said two separate passages is adapted to vent to atmosphere immediately adjacent to the corresponding nare.

19. A user interface as claimed in claim 14 wherein only said second passage of said two separate passages is adapted to vent to atmosphere immediately adjacent to the corresponding nare.

* * * * *